(12) United States Patent
Olsson

(10) Patent No.: US 11,719,813 B2
(45) Date of Patent: *Aug. 8, 2023

(54) ULTRASONIC DIAGNOSTIC IMAGING SYSTEM WITH SPATIAL COMPOUNDING OF TRAPEZOIDAL SECTOR

(71) Applicant: KONINKLIJKE PHILIPS N.V., Eindhoven (NL)

(72) Inventor: Lars Jonas Olsson, Woodinville, WA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 397 days.

This patent is subject to a terminal disclaimer.

(21) Appl. No.: 16/424,808

(22) Filed: May 29, 2019

(65) Prior Publication Data
US 2019/0310367 A1    Oct. 10, 2019

Related U.S. Application Data

(63) Continuation of application No. 14/778,292, filed as application No. PCT/IB2014/060079 on Apr. 24, 2014, now Pat. No. 10,345,444.

(Continued)

(51) Int. Cl.
*G01S 15/89* (2006.01)
*G01S 7/52* (2006.01)
(Continued)

(52) U.S. Cl.
CPC ............ *G01S 15/8995* (2013.01); *A61B 8/14* (2013.01); *A61B 8/4444* (2013.01);
(Continued)

(58) Field of Classification Search
CPC ............ G01S 15/8918; G01S 15/8925; G01S 15/8995; G01S 7/52085; A61B 8/488;
(Continued)

(56) References Cited

U.S. PATENT DOCUMENTS 4,159,462 A   6/1979   Rocha et al.
4,245,250 A   1/1981   Tiemann
(Continued)

FOREIGN PATENT DOCUMENTS

EP   1906207 A1   4/2008
JP   2004154567 A   6/2004
WO   2007099474 A1   9/2007

OTHER PUBLICATIONS

O'Donnell "Optimum Displacement for Compound Image Generation in Medical Ultrasound" IEEE Transactions on Ultrasonics, Ferroelectrics, and Frequency Control, vol. 35, No. 4, Jul. 1988 pp. 47-476.

*Primary Examiner* — Bo Joseph Peng

(57) ABSTRACT

An ultrasonic diagnostic imaging system produces spatially compounded trapezoidal sector images by combining component frames acquired from different look directions. A virtual apex scan format is used such that each scanline of a component frame emanates from a different point on the face of an array transducer and is steered at a different scanning angle. For different component frames the scanlines are steered at respectively different angles. In an illustrated example, the scanlines of each component frame are incremented by five degrees relative to the corresponding scanlines in a reference component frame. When the component frames are combined for spatial compounding, the maximum number of component frames are combined over virtually the entire image field.

8 Claims, 6 Drawing Sheets

Related U.S. Application Data

(60) Provisional application No. 61/804,783, filed on Mar. 25, 2013.

(51) Int. Cl.
*A61B 8/14* (2006.01)
*A61B 8/00* (2006.01)
*A61B 8/08* (2006.01)

(52) U.S. Cl.
CPC ............ *A61B 8/4494* (2013.01); *A61B 8/461* (2013.01); *A61B 8/488* (2013.01); *A61B 8/5207* (2013.01); *A61B 8/5238* (2013.01); *G01S 7/52085* (2013.01); *G01S 15/8918* (2013.01); *G01S 15/8925* (2013.01)

(58) Field of Classification Search
CPC ..... A61B 8/461; A61B 8/5238; A61B 8/5207; A61B 8/4444; A61B 8/4494; A61B 8/14
See application file for complete search history.

(56) References Cited

U.S. PATENT DOCUMENTS

| | | |
|---|---|---|
| 4,319,489 A | 3/1982 | Yamaguchi et al. |
| 4,649,327 A | 3/1987 | Fehr et al. |
| 51,234,151 | 6/1992 | Daigle |
| 5,485,842 A | 1/1996 | Quistgaard |
| 5,860,924 A | 1/1999 | Quistgaard |
| 6,126,598 A | 10/2000 | Entrekin et al. |
| 6,210,328 B1 | 4/2001 | Robinson et al. |
| 6,224,552 B1 | 5/2001 | Jago et al. |
| 6,416,477 B1 | 7/2002 | Jago |
| 2004/0054284 A1* | 3/2004 | Cai ................... G01S 7/52034 600/443 |
| 2006/0293596 A1* | 12/2006 | Jago ................... G01S 7/52093 600/437 |
| 2008/0208061 A1* | 8/2008 | Halmann ............ G01S 15/8995 600/459 |
| 2009/0016163 A1 | 1/2009 | Freeman et al. |
| 2009/0069681 A1 | 3/2009 | Lundberg et al. |

\* cited by examiner

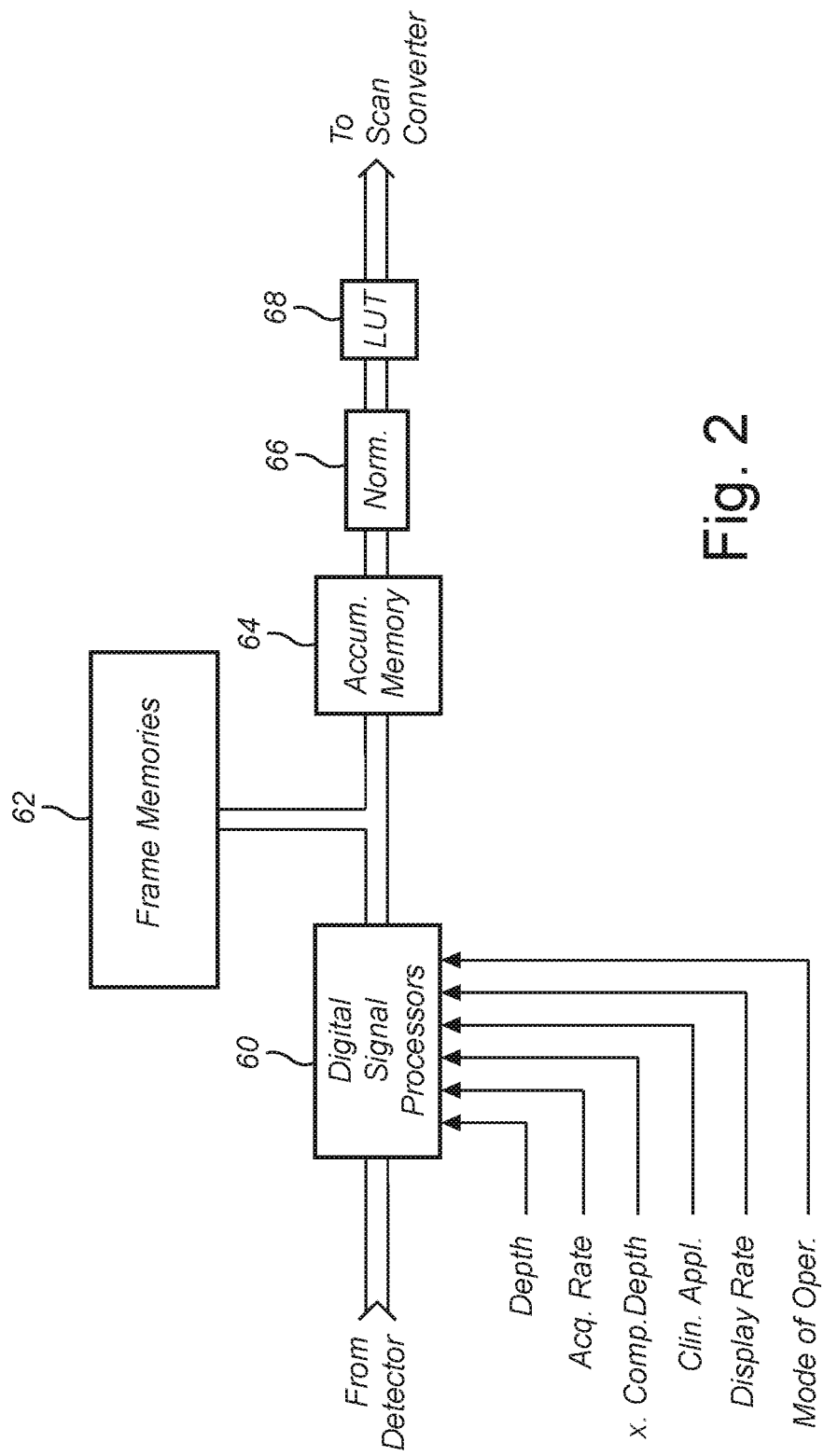

ULTRASONIC DIAGNOSTIC IMAGING SYSTEM WITH SPATIAL COMPOUNDING OF TRAPEZOIDAL SECTOR

RELATED APPLICATIONS

This application is a continuation of U.S. application Ser. No. 14/778,292, filed on Sep. 18, 2015, which is the U.S. National Phase application under 35 U.S.C. § 371 of International Application No. PCT/IB2014/060079, filed on Mar. 24, 2014, which claims the benefit of U.S. application Ser. No. 61/804,783, filed on Mar. 25, 2013. These applications are hereby incorporated by reference herein.

This invention relates to ultrasonic diagnostic imaging systems and, in particular, to ultrasonic diagnostic imaging systems which produce spatially compounded images in a trapezoidal sector format.

Spatial compounding is an imaging technique in which a number of ultrasound images of a given target that have been obtained from multiple vantage points or angles (look directions) are combined into a single compounded image by combining the data received from each point in the compound image target which has been received from each angle or look direction. Examples of spatial compounding may be found in U.S. Pat. No. 4,649,327 (Fehr et al.); U.S. Pat. No. 4,319,489 (Yamaguchi et al.); U.S. Pat. No. 4,159,462 (Rocha et al.); U.S. Pat. No. 6,210,328 (Robinson et al.) U.S. Pat. No. 6,126,598 (Entrekin et al.) and U.S. Pat. No. 6,224,552 (Jago et al.) Real time spatial compound imaging is performed by rapidly acquiring a series of partially overlapping component image frames from substantially independent spatial directions, utilizing an array transducer to implement electronic beam steering and/or electronic translation of the component frames. The component frames are combined into a compound image by summation, averaging, peak detection, or other combinational means. The acquisition sequence and formation of compound images are repeated continuously at a rate limited by the acquisition frame rate, that is, the time required to acquire the full complement of scanlines of the component frames over the selected width and depth of imaging. The compounded image typically shows lower speckle and better specular reflector delineation than conventional ultrasound images from a single viewpoint. Speckle is reduced (i.e., speckle signal to noise ratio is improved) by the square root of N in a compound image with N component frames, provided that the component frames used to create the compound image are substantially independent and are averaged. Several criteria can be used to determine the degree of independence of the component frames (see, e.g., O'Donnell et al. in IEEE Trans. UFFC v. 35, no. 4, pp 470-76 (1988)). In practice, for spatial compound imaging with a steered linear array, this implies a minimum steering angle between component frames. This minimum angle is typically on the order of several degrees, e.g., three or four degrees.

The second way that spatial compound scanning improves image quality is by improving the acquisition of specular interfaces. For example, a curved bone-soft tissue interface produces a strong echo when the ultrasound beam is exactly perpendicular to the interface, and a very weak echo when the beam is only a few degrees off perpendicular. These interfaces are often curved, and with conventional scanning only a small portion of the interface is visible. Spatial compound scanning acquires views of the interface from many different angles, making the curved interface visible and continuous over a larger field of view. Greater angular diversity generally improves the continuity of specular targets. However, the angular diversity available is limited by the acceptance angle of the transducer array elements. The acceptance angle depends on the transducer array element pitch, frequency, and construction methods.

Spatial compounding can be done in the various image formats used in ultrasonic imaging including sector images and linear images. A convenient format for spatial compounding is the steered linear format as described in the aforementioned Robinson et al., Entrekin et al., and Jago et al. patents. In this format each component frame is formed from parallel scanlines steered in a given look direction. For example, a first component frame can be acquired using scanlines all steered in the 0° (straight ahead) direction. Second and third component frames can then be acquired with all scanlines steered in the +15° direction and the −15° direction, respectively. When the component frames are combined in spatial alignment they will produce a trapezoidal-shaped image which is spatially compounded. Unfortunately, as discussed below, the spatial compounding effect is not uniform throughout the image. This is because there are different degrees of image overlap in different areas of the combined image. Accordingly it is desirable to do spatial compounding in a trapezoidal scan format in which the spatial compounding effect combines the greatest number of component frames throughout the largest extent of the spatially compounded image.

In accordance with the principles of the present invention, spatially compounded trapezoidal images are formed by scanning virtual apex component frames. Virtual apex is a phased beam steering technique in which the scanlines that scan the image field are steered at different angles. It is called virtual apex because all of the scanlines appear to emanate from a common point or apex behind the face of the ultrasound transducer. Component frames are acquired in the virtual apex format with the scanlines steered at differing angles relative to the face of the transducer in each component frame. When the component frames are combined the overlap over a substantial portion of the image field, providing a high degree of spatial compounding throughout a large region of the compounded image.

In the drawings:

FIG. 2 illustrates in block diagram form an implementation of the spatial compounding processor of FIG. 1;

Figure 1:
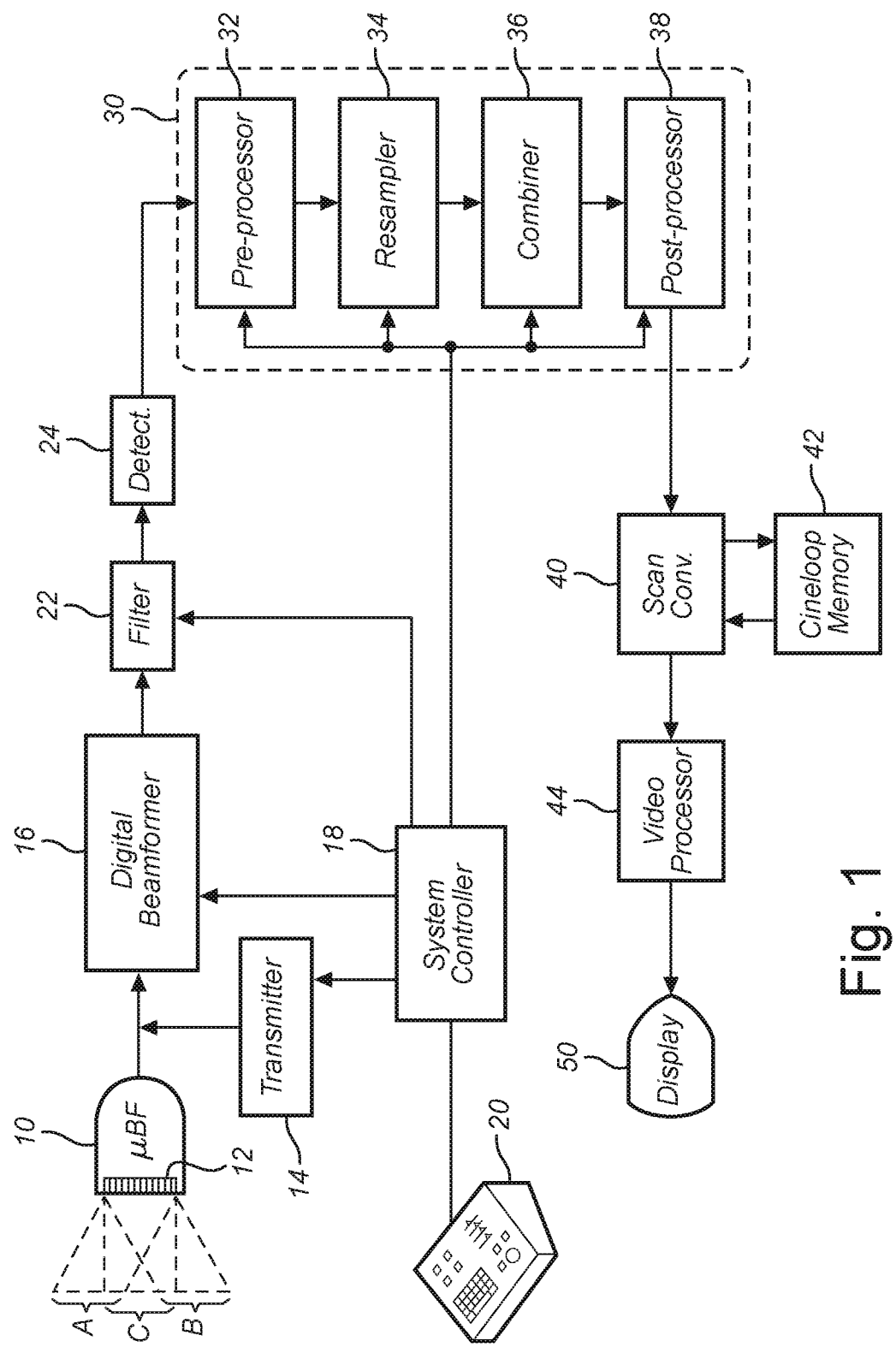
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown. An ultrasound probe 10 including a planar array transducer 12 which transmits beams at different angles over an image field denoted by the dashed rectangle and parallelograms outlining regions scanned by steered linear beam scanning. Three groups of scanlines are indicated in the drawing, labeled A, B, and C with each group being steered at a different angle relative to the face of the array transducer. The array transducer can be a one dimensional (1D) array of transducer elements or a two dimensional (2D) matrix array of transducer elements. The transmission of the beams is controlled by a transmitter 14 which controls the phasing and time of actuation of each of the elements of the array transducer so as to transmit each beam from a predetermined origin along the array and at a predetermined angle. When a 2D array transducer is used, transmission and partial beamforming is provided by a microbeamformer IC (µBF) located in the probe 10. A 1D array transducer can also use a microbeamformer if desired. The echoes returned from along each scanline are received by the elements of the array, digitized as by analog to digital conversion, and coupled to a digital beamformer 16. When a microbeamformer is used, at least partial beamforming is performed in the probe by the microbeamformer before the signals are coupled to the system beamformer 16. The digital beamformer delays and sums the echoes from the array elements or microbeamformer to form a sequence of focused, coherent digital echo samples along each scanline. The transmitter 14, microbeamformer and beamformer 16 are operated under control of a system controller 18, which in turn is responsive to the settings of controls on a user interface 20 operated by the user of the ultrasound system. The system controller controls the transmitter (and/or microbeamformer) to transmit the desired number of scanline groups at the desired angles, transmit energies and frequencies. The system controller also controls the digital beamformer to properly delay and combine the received echo signals for the apertures and image depths used.

The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are assembled for each point in the image and are Doppler processed to estimate the Doppler shift or Doppler power intensity.

In accordance with the principles of the present invention the digital echo signals are processed by spatial compounding in a processor 30. The digital echo signals are initially pre-processed by a preprocessor 32. The pre-processor 32 can preweight the signal samples if desired with a weighting factor. The samples can be preweighted with a weighting factor that is a function of the number of component frames used to form a particular compound image. The pre-processor can also weight edge lines that are at the edge of one overlapping image so as to smooth the transitions where the number of samples or images which are compounded changes. The pre-processed signal samples may then undergo a resampling in a resampler 34. The resampler 34 can spatially realign the estimates of one component frame or to the pixels of the display space.

After resampling the image frames are compounded by a combiner 36. Combining may comprise summation, averaging, peak detection, or other combinational means. The samples being combined may also be weighted prior to combining in this step of the process. Finally, post-processing is performed by a post-processor 38. The post-processor normalizes the combined values to a display range of values. Post-processing can be most easily implemented by look-up tables and can simultaneously perform compression and mapping of the range of compounded values to a range of values suitable for display of the compounded image.

The compounding process may be performed in estimate data space or in display pixel space. In a preferred embodiment scan conversion is done following the compounding process by a scan converter 40. The compound images may be stored in a Cineloop® memory 42 in either estimate or display pixel form. If stored in estimate form the images may be scan converted when replayed from the Cineloop memory for display. The scan converter and Cineloop memory may also be used to render three dimensional presentations of the spatially compounded images as described in U.S. Pat. Nos. 5,485,842 and 5,860,924. Following scan conversion the spatially compounded images are processed for display by a video processor 44 and displayed on an image display 50.

FIG. 2 illustrates one implementation of the spatial compounding processor 30 of FIG. 1. The processor 30 in this example is implemented by one or more digital signal processors 60 which process the image data in various ways. The digital signal processors 60 weights the received image data and can resample the image data to spatially align pixels from frame to frame, for instance. The digital signal processors 60 direct the processed image frames to a plurality of frame memories 62 which buffer the individual component image frames. The number of component image frames capable of being stored by the frame memories 62 is preferably at least equal to the maximum number of component image frames to be compounded such as sixteen frames. In accordance with the principles of the present invention, the digital signal processors are responsive to control parameters including image display depth, depth of region of greatest compounding, clinical application, compound display rate, mode of operation, and acquisition rate for determining the number of images to compound at a given instant in time. The digital signal processors select component frames stored in the frame memories 62 for assembly as a compound image in accumulator memory 64. The compounded image formed in the accumulator memory 64 is weighted or mapped by a normalization circuit 66, then compressed to the desired number of display bits and, if desired, remapped by a lookup table (LUT) 68. The fully processed compounded image data is then transmitted to the scan converter for formatting and display.

Figure 3B:
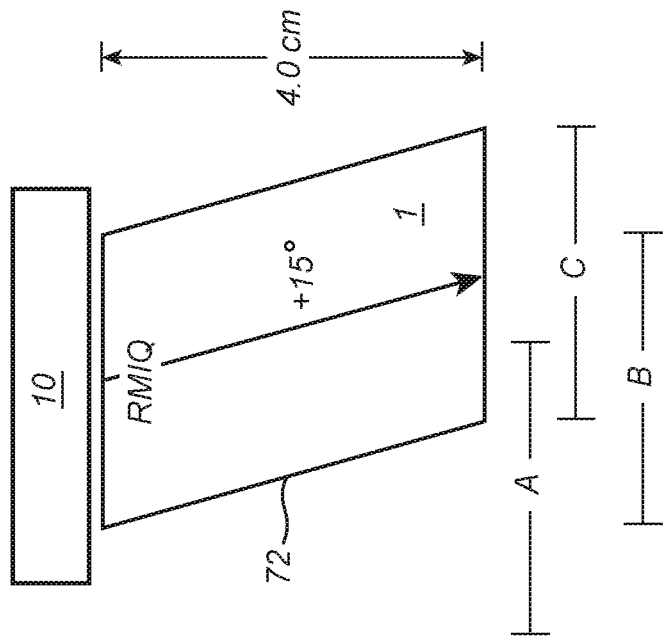
FIGS. 3a through 3d illustrate the region of maximum image quality of a spatially compounded image formed by component frames acquired in the steered linear scan format.

Compound scanning with a steered linear array results in a pattern of overlapping component frames such that the region of maximum image quality (RMIQ) where all N frames overlap is an inverted triangular region with its base at the top of the compound image. With other scanning geometries such as overlapping phased array frames emanating from different points of the array, the RMIQ will exhibit a correspondingly different shape. This is illustrated by FIGS. 3a through 3d. FIGS. 3b, 3c, and 3d illustrate component steered linear frames which are combined to form the spatially compounded image of FIG. 3a. The component frame of FIG. 3b is formed by a plurality of parallel, adjacent scanlines which scan the parallelogram-shaped image field 72 at an angle of +15°, one of which is shown in the center of the image frame 72. This is component frame "C" of the compounded image. The component frame of FIG. 3c is formed by a plurality of parallel, adjacent scanlines which scan the rectangular-shaped image field 74 at an angle of 0°, one of which is shown in the center of the image frame 74. This is component frame "B" of the compounded image. The component frame of FIG. 3d is formed by a plurality of parallel, adjacent scanlines which scan the parallelogram-shaped image field 76 at an angle of −15°, one of which is shown in the center of the image frame 76. This is component frame "A" of the compounded image.

Figure 3A:
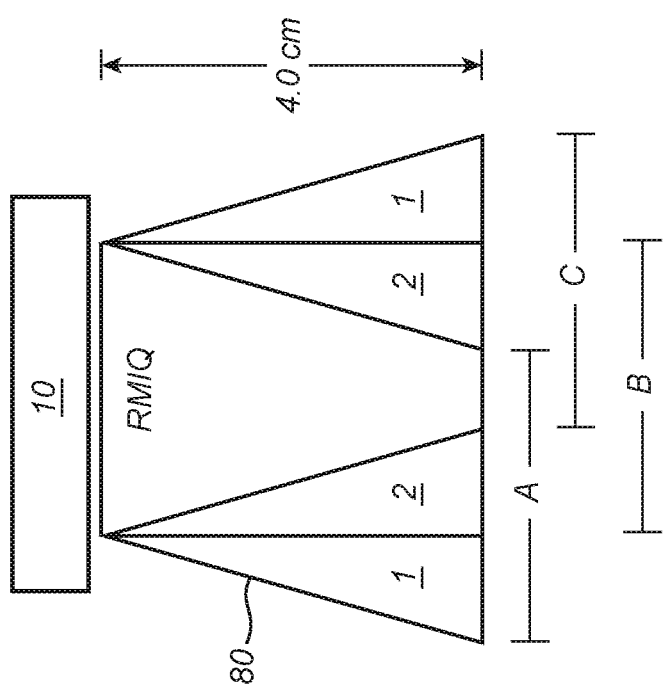
Figure 3D:
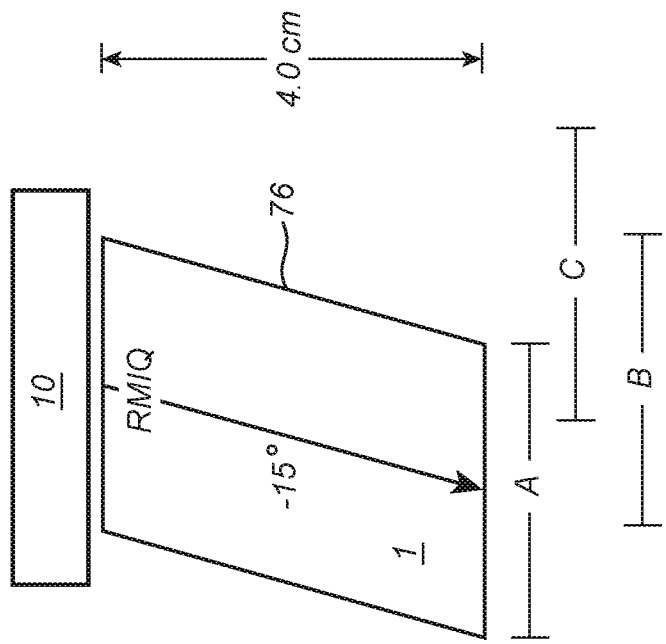
Figure 3C:
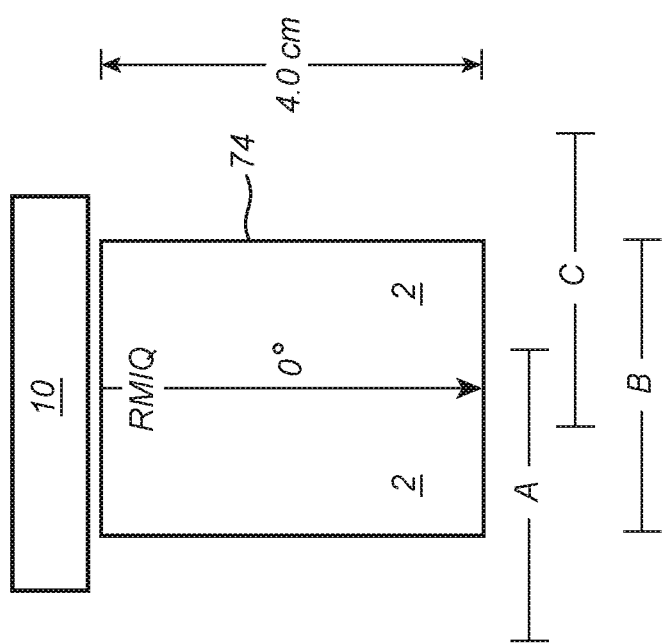

In FIG. 3a the three component frames A, B, and C are shown when spatially registered to form the final compounded image 80. On either side of the RMIQ region, where all three component frames overlap and are compounded, the number of overlapping frames decreases spatially, with only two frames overlapping in the regions designated 2 and single frames present in the regions designated 1. This means that a particular point in the compounded image may only receive contributions from a sub-set of the component frames, depending on whether a component frame has data at that point.

Figure 4A:
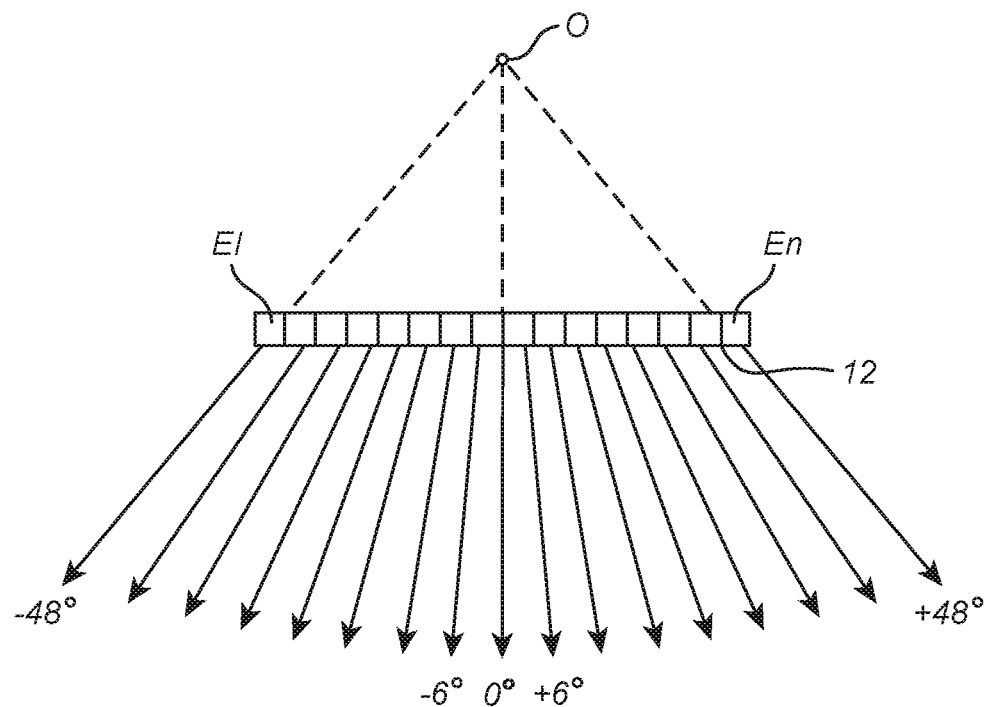
FIGS. 4a through 4c illustrates component frames acquired for formation of a spatially compounded trapezoidal image in accordance with the present invention.

In accordance with the principles of the present invention a spatially compounded ultrasound image is produced from component frames scanned in a virtual apex scan format. Virtual apex is a form of phased array scanning in which the beams are steered at progressively different angles relative to the face (emitting surface) of the transducer array. In conventional phased array imaging all of the beams emanate from a common point on the face of the array, generally at the center of the array. This common point is the apex of a triangular-shaped sector image. In virtual apex scanning the common point from which the scanlines emanate is a "virtual" point located behind the face of the array as described in U.S. Pat. No. 5,123,415 (Daigle). Such a scan format is shown in FIG. 4a, where the virtual apex is the point "0" behind the face of the array 12. The transducer array in this example is a linear 1D array, a single line of transducer elements E1 to En. As is seen in this example the center scanline is transmitted and received at an angle of 0° relative to the face of the array. The angle convention used in ultrasound scanning designates the straight-ahead direction in front of the array as the 0° direction. On either side of this center scanline the adjacent scanlines are progressively steered at ever-increasing angles. In this example the scanline immediately to the left of center is steered at an angle of –6° and the scanline immediately to the right of center is steered at an angle of +6°. The inclination of steering angles increases in increments of 6° with increasing distance from the center of the array to a maximum scanline angle of –48° and +48° at the lateral sides of the scanned sector-shaped image field.

Figure 4B:
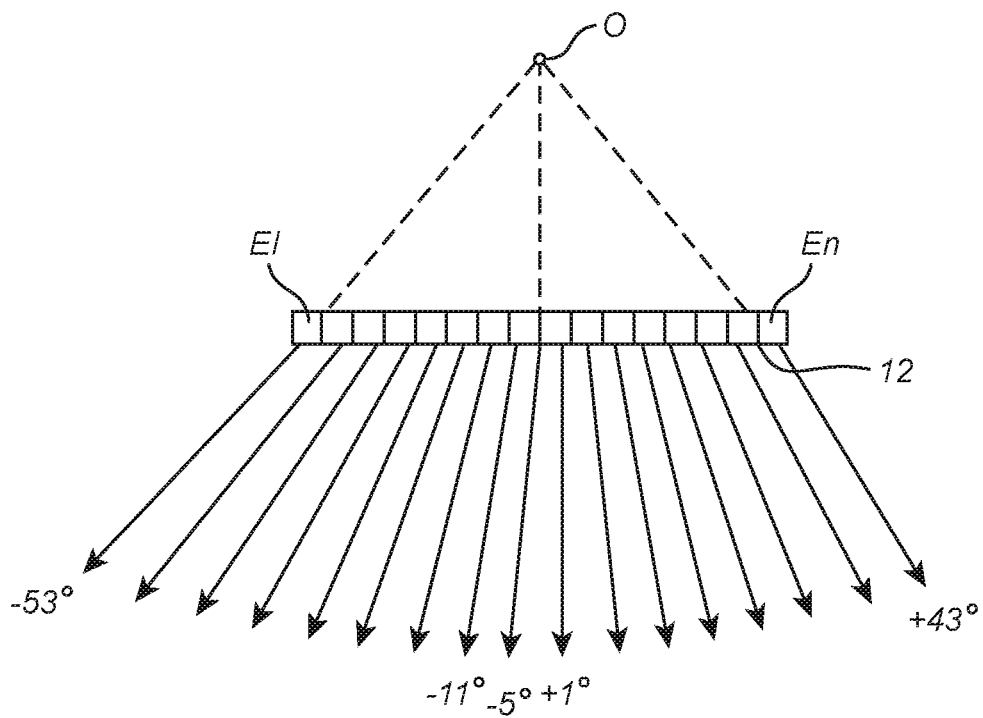
Figure 4C:
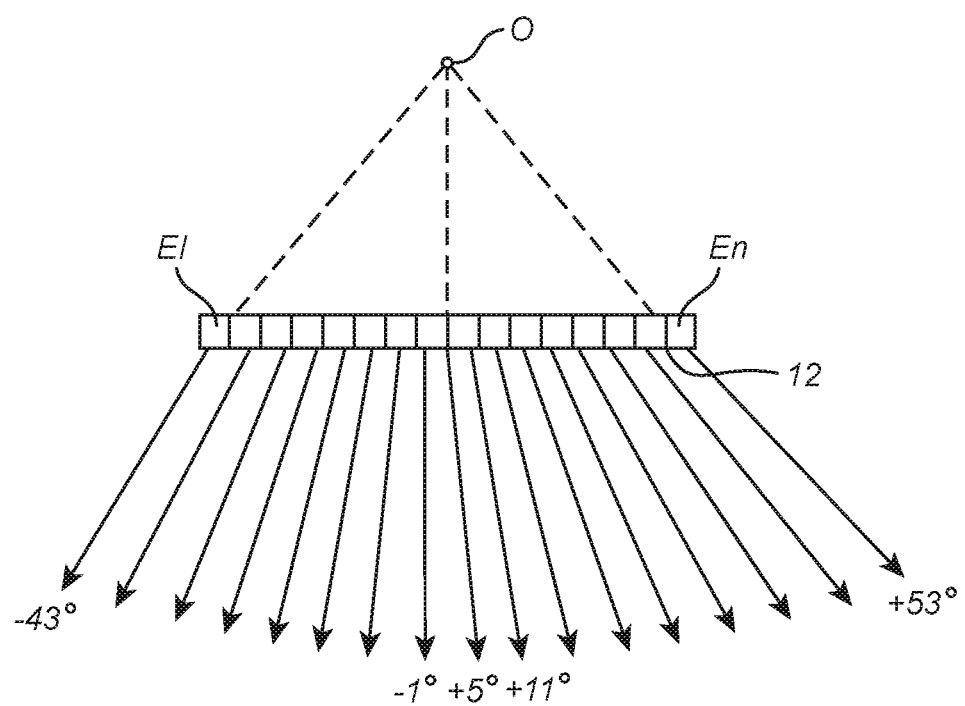

The scan format of FIG. 4a produces one component frame for spatial compounding in this example. Two other component frames are shown in FIGS. 4b and 4c. In FIG. 4b each scanline emanates from the same point on the face of the array as the scanlines in FIG. 4a, but are steered in different look directions of 5° to the left. The scanline which was steered at an angle of 0° in FIG. 4a is steered at an angle of –5° in FIG. 4b. This scanline now interrogates the image field in a different look direction than the 0° scanline of FIG. 4a. The 5° difference in look direction provides a diversity in look direction sufficient to produce the speckle reduction characteristic of a spatially compounded image. Similarly, the scanline to the left of center which was formerly steered at an angle of –6° is now steered an addition increment of 5° so that it is directed at an angle of –11°. The scanline to the right of center, formerly steered at an angle of +6°, is now steered at an angle of +1°. This incremental change in steering angles is carried out across the image field and the scanline to the left lateral side of the sector is steered at an angle of –53° and the scanline on the right lateral side is steered at an angle of +43°. Thus, each point in the image field in FIG. 4b is interrogated from a different look direction than that effected by the scan format of FIG. 4a.

In FIG. 4c each scanline again emanates from the same point on the face of the array as in the previous component frames, but this time at an angular increment of 5° to the right. Thus, the 0° scanline of FIG. 4a is now steered at an angle of +5°. The scanline to the left of center that was steered at an angle of –6° in FIG. 4a is now steered at an angle of –1° in FIG. 4c, and the scanline to the right that was steered at an angle of +6° is now steered at an angle of +11°. This 5° incremental inclination of each scanline is repeated across the image field, resulting in the left-most scanline being steered at a –43° angle and the right-most scanline being steered at an angle of +53°. This results in each point in the image field being interrogated at a third look direction which is different from that of both the first and second component images.

When the three component images of FIGS. 4a, 4b, and 4c are compounded, there is a compounding of three component images across virtually the entire area of the image. Stated another way, the RMIQ exists over virtually the entire image field. It is only at the lateral extremes of the image where the RMIQ falls off. The inventive spatial compounding technique is effective for both two and three dimensional imaging, it can be performed with both standard phased array scanning and virtual apex phased scanning, and it can be performed with scan converted or pre-scan converted image data. While it is generally more convenient to acquire each component frame in its entirety before scanning another component frame, those skilled in the art will recognize that the scanlines of different component frames can be acquired in a time-interleaved manner. For example, a scanline emanating from one point on the face of the array can be acquired in a first look direction for one component frame, a scanline emanating from the same point can be acquired in a second look direction for a second component frame, and a scanline emanating from the same point can be acquired in a third look direction for a third component frame. The component frames are then assembled from these time-interleaved scanlines.

What is claimed is:
1. An ultrasound system for producing a spatially compounded image, the system including:
   a probe comprising an ultrasound array; and
   at least one processor in communication with the ultrasound array, the processor configured to:
   control the ultrasound array to acquire scanlines for generating a plurality of component image frames, wherein each of the plurality of component image frames comprises a look direction and originates from a plurality of scanlines emanating from the ultrasound array from a common apex,
   wherein the look direction of a component image frame corresponds to an angular range of the scanlines with respect to the common apex, and the look direction of each of the plurality of component image frames is overlapping and different from the look direction of another one of the plurality of component image frames such that each point in the spatially compounded image includes scanlines from at least three component image frames, and
   wherein said controlling causes the ultrasound array to acquire the scanlines in a time-interleaved manner by causing the ultrasound array to:
   acquire a first plurality of scanlines during a first time interval, each of the first plurality of scanlines emanating from a first point on a face of the array, in each of the different look directions, and
   acquire a second plurality of scanlines during a second time interval, each of the second plurality of scanlines emanating from a second point on the face of the array, in each of the different look directions, wherein the second time interval is after the first time interval; and generate the spatially compounded image from the plurality of component image frames.

2. The ultrasound system of claim 1, further comprising a beamformer associated with the probe and the processor, the beamformer configured to receive signals corresponding to the plurality of scanlines.

3. The ultrasound system of claim 1, wherein the plurality of look directions comprise a first look direction, a second look direction and a third look direction, and wherein the angular range of the first and third look directions differ to the left and right, respectively, from the angular range of the second look direction.

4. The ultrasound system of claim 3, wherein an angular increment between the first look direction, the second look direction, and the third look direction is at least 5 degrees.

5. The ultrasound system of claim 1, wherein the common apex is located behind a face of the ultrasound array.

6. The ultrasound system of claim 1, wherein the ultrasound array is a one-dimensional or a two-dimensional array.

7. The ultrasound system of claim 1, wherein the spatially compounded image is generated by combining the component image frames by one of summation, averaging, and peak detection.

8. A method of generating a spatially compounded image, the method comprising:

controlling an ultrasound array, via at least one processor, to generate a plurality of component image frames to form the spatially compounded image, wherein each component image frame comprises a look direction and originates from a plurality of scanlines emanating from the ultrasound array at an angle from a common apex, the look direction of a component image frame corresponds to an angular range of the scanlines with respect to the common apex, and the look direction of each component image frame is overlapping and different from the look direction of another component image frame such that each point in the compounded image includes scanlines from at least three component image frames, and said controlling causes the ultrasound array to acquire the scanlines in a time-interleaved manner by:

acquiring a first plurality of scanlines during a first time interval, each of the first plurality of scanlines emanating from a first point on a face of the array, in each of the different look directions, and acquiring a second plurality of scanlines during a second time interval, each of the second plurality of scanlines emanating from a second point on the face of the array, in each of the different look directions, wherein the second time interval is after the first time interval; and generating, via the at least one processor, the spatially compounded image from the plurality of component image frames.

* * * * *